US00PP23920P2

(12) United States Plant Patent
Straver

(10) Patent No.: US PP23,920 P2
(45) Date of Patent: Sep. 24, 2013

(54) ***CLEMATIS* PLANT NAMED 'ZOQUM'**

(50) Latin Name: ***Clematis* hybrid**
Varietal Denomination: Zoqum

(75) Inventor: Willem Straver, Emmerich (DE)

(73) Assignee: J. Van Zoest Beheer B.V., Boskoop (NL)

( * ) Notice: Subject to any disclaimer, the term of this patent is extended or adjusted under 35 U.S.C. 154(b) by 42 days.

(21) Appl. No.: 13/374,146

(22) Filed: Dec. 14, 2011

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Kent L Bell
(74) *Attorney, Agent, or Firm* — Penny J. Aguirre

(57) ABSTRACT

A new cultivar of *Clematis* named 'Zoqum', characterized by its free-flowering habit with bell-shaped flowers that are of red-purple in color and non-fading, its near sterility, a climbing plant habit and its cold hardiness to at least U.S.D.A. Zone 5.

2 Drawing Sheets

Botanical classification: *Clematis* hybrid.
Variety denomination: 'Zoqum'.

BACKGROUND OF THE INVENTION

The present invention relates to a new and distinct cultivar of *Clematis* of hybrid origin (Viticella Group) and will be referred to hereafter by its cultivar name 'Zoqum'. 'Zoqum' is grown as an herbaceous climbing plant for use in the landscape or as a flowering potted plant for the terrace.

'Zoqum' was derived from an ongoing breeding program by the Inventor at his nursery in Emmerich, Germany. The goal of the selection was to select a hardy climber with uniquely colored flowers that could be grown for different purposes in the garden.

'Zoqum' was selected in 2007 as a single unique plant and arose from a cross made in 2003. The Inventor did not keep the records on the proprietary seedlings used for the cross, therefore the parentage is unknown.

Asexual reproduction of the new cultivar was first accomplished by internodial stem cuttings under the direction of the Inventor in Boskoop, The Netherlands. The characteristics of this cultivar have been determined to be stable and are reproduced true to type in successive generations.

SUMMARY OF THE INVENTION

The following traits have been repeatedly observed and represent the characteristics of the new cultivar as grown outdoors and observed for five years in Boskoop, The Netherlands. These attributes in combination distinguish 'Zoqum' from other cultivars of *Clematis* known to the Inventor.

1. 'Zoqum' exhibits a very floriferous habit.
2. 'Zoqum' has bell-shaped flowers that are red-purple in color.
3. 'Zoqum' has flowers that are not fading.
4. 'Zoqum' is considered sterile; seeds are very rarely produced.
5. 'Zoqum' has a climbing plant habit.
6. 'Zoqum' is at least cold hardy to U.S.D.A. Zone 5.

'Zoqum' can be compared to the cultivar 'Etoile Rose' (unpatented) and 'Odoriba' (unpatented). 'Zoqum' exhibits flowers that are red-purple in color with a closed bell-shape flower and a glabrous flower bud.

*Clematis* 'Etoile Rose' differs from 'Zoqum' in having flowers that are red-pink with white in color, an open bell-shape flower and a more hairy flower bud.

*Clematis* 'Odoriba' differs from 'Zoqum' in having flowers that are red-purple which are half white in color at the upper surface, an open bell-shape flower and sparsely hairy flower bud.

BRIEF DESCRIPTION OF THE DRAWING

The accompanying colored photographs illustrate the overall appearance and distinct characteristics of the new *Clematis*. The photographs were taken of a three year-old plant of 'Zoqum' as grown in a one-gallon container in Boskoop, The Netherlands.

The photograph in FIG. 1 shows the flowering habit.

Figure 1:
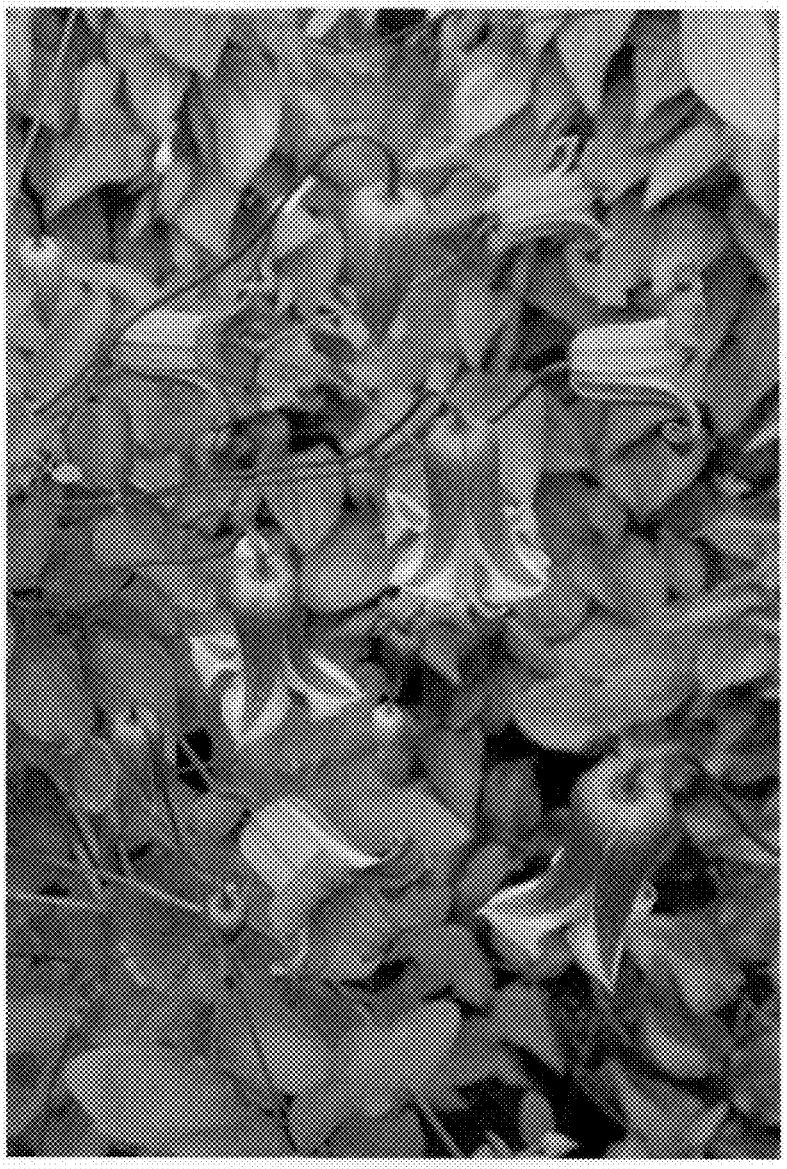
Figure 2:
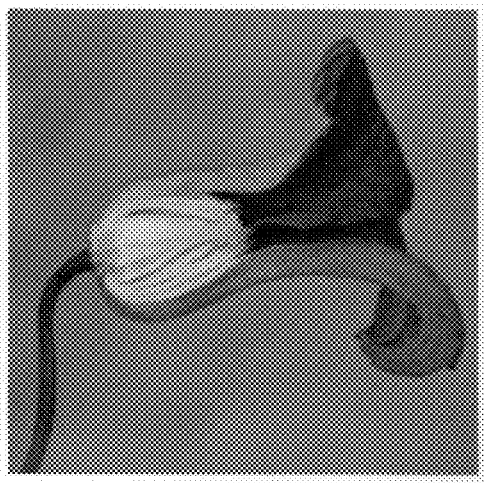

The photograph in FIG. 2 shows the inside of the flower with a close up of the stamens and pistils.

Figure 3:
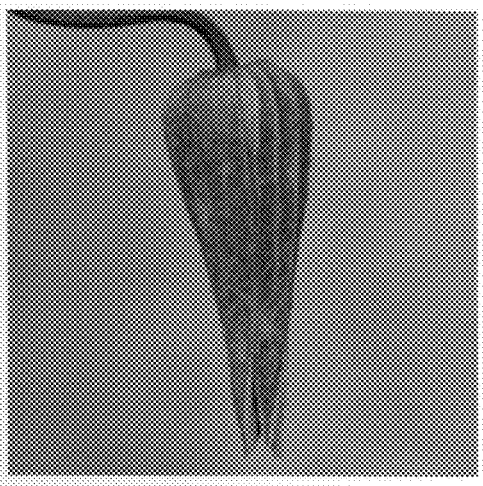

The photograph in FIG. 3 shows the flower bud.

Figure 4:
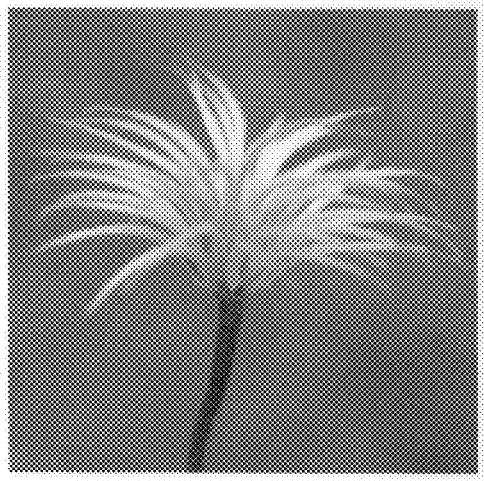

FIG. 4 shows an immature seedhead.

Figure 5:
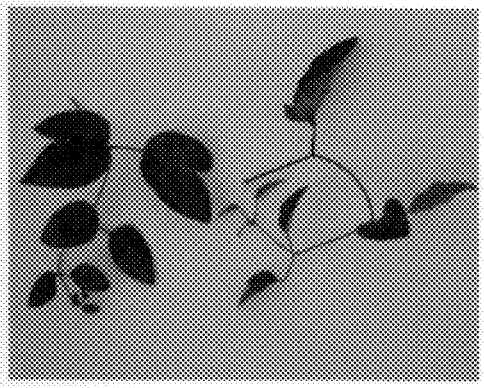

FIG. 5 shows 2 leaves.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of three year-old plants of 'Zoqum' as grown outdoors in one-gallon containers under full sun at a nursery in Boskoop, The Netherlands. The phenotype of the new cultivar may vary with variations in environmental, climatic, and cultural conditions, as it has not been tested under all possible environmental conditions. The color determination is in accordance with The 2001 R.H.S.

Colour Chart of the Royal Horticultural Society, London, England, except where general color terms of ordinary dictionary significance are used.

General description:

*Botanical classification.*—*Clematis* 'Zoqum' (classified in the Viticella Group).

*Blooming period.*—Main flowering period of 6 to 8 weeks in summer.

*Plant habit.*—Herbaceous climber.

*Height and spread.*—Three year-old plant will be at about 2 m height when pruned in late winter at 25 cm above soil level and about 60 cm in width.

*Cold hardiness.*—At least to U.S.D.A. Zone 5.

*Culture.*—Moist but well-drained soils in full sun with roots shaded.

*Diseases.*—No comparison trials have been conducted to date in regards to powdery mildew susceptibility or resistance.

*Root description.*—Fleshy.

Growth and propagation:

*Propagation.*—Internodial softwood cuttings from vegetative shoots.

*Root initiation.*—Roots develop in 6 weeks in summer under greenhouse conditions.

*Time required for root development.*—75 to 90 days to develop a 5 cm container from a 5 cm cutting.

*Growth rate.*—Moderately vigorous once planted in the landscape.

Stem description:

*Shape.*—Round and 6 ribbed.

*Stem color.*—166A.

*Stem size.*—About 2 m (including peduncle and terminal pedicel) in length, an average of 3 mm in diameter.

*Stem surface.*—Mainly glabrous with a few scattered hairs.

*Internode length.*—Ranges from 5 to 15 cm.

*Branching.*—Basal branching.

Foliage description:

*Leaf arrangement.*—Opposite.

*Leaf division.*—Compound; pinnate, an average of 9 leaflets per leaf.

*Leaf shape.*—Roughly ovate in shape.

*Leaf size.*—An average of 12 cm in length and width.

*Leaflet shape.*—Ovate.

*Leaflet base.*—Oblique.

*Leaflet apex.*—Acute.

*Leaflet fragrance.*—No particular fragrance when crushed.

*Leaflet venation.*—Slightly reticulate on both surfaces.

*Leaflet margins.*—Entire, lower leaflet sometimes lobed.

*Leaflet attachment.*—Articulate, 147A, glabrous but a few scattered hairs.

*Leaflet surface.*—Glabrous on both surfaces.

*Leaflet size.*—Up to 6 cm in length and 4 cm in width.

*Leaflet color.*—Upper surface 147A, lower surface 146B.

*Petioles.*—Average of 4 cm in length and 1 mm in width, 187A in color, sparsely pubescent surface.

*Petiolules.*—Average of 1.2 cm in length and 1 mm in width, 187A in color, sparsely pubescent surface.

Inflorescence description:

*Inflorescence type.*—Usually a 3 flowered dichasial cyme.

*Inflorescence arrangement.*—Terminal and axillary on young shoots.

*Pedicels.*—Up to 8 cm in length and an average of 2 cm, 147A flushed with 79A in color, surface glabrous and round in shape.

*Peduncles.*—Average of 2 cm in length and 2.5 cm in width, 147A flushed with 79A in color, surface glabrous and round in shape.

*Peduncle bracts.*—Leaf-like, division simple, about 4 cm in length and 3 cm in width, color and surface is the same as leaflets.

*Bud description.*—Downward facing, lanceolate in shape, 59C in color, apex acuminate in shape and quickly opening, glabrous surface, up to 4 cm in length and 2.5 cm in width.

*Flower fragrance.*—None.

*Lastingness of flowers.*—Individual flowers last about 7 days, the tepals are caducous followed by the stamens.

*Flower quantity.*—Terminal and axillary on young shoots, on a 3 year old plant about 30 to 60 flowers per stem.

*Flower type.*—Single, urceolate with campanulate apex in shape.

*Flower aspect.*—Downward facing.

*Flower size.*—Up to 4 cm in length and 4 cm in diameter.

*Tepal number.*—4.

*Tepal shape.*—Spathulate.

*Tepal apex.*—Acute and curled outwards.

*Tepal base.*—Oblong.

*Tepal margins.*—Entire or slightly crenulate at apex.

*Tepal surface.*—Upper surface; glabrous, lower surface; glabrous with villous margin.

*Tepal color.*—Upper surface; a blend of 72A and 72B with middle section 61B and base paler than 61B, lower surface; 72A with margin closest to 155A and villous.

*Tepal size.*—Up to 5 cm in length and 2 cm in width.

Reproductive organs:

*Gynoecium.*—Numerous pistils (up to 30) 1.4 cm in length; ovary white hairy (about 155A); style 145D in color and plumose and 155A in color at the base, about 1 cm in length; stigma 145D in color, glabrous and curled.

*Androcoecium.*—Filaments 0.4 to 1 cm in length, 0.1 cm in width, linear in shape, 4D in color, surface glabrous but a few hairs below the anther; anthers 5 mm in length, linear in shape, 11D in color; connective just a bit obtuse elongated, surface hairy, 4D in color.

*Seed.*—Head up to 4 cm in diameter, seed development is very rare, when mature; ovary portion 202A in color and hairy; style portion plumose, 202A in color and 2 cm in length; stigma portion 202A in color and hooked.

It is claimed:

1. A new and distinct cultivar of *Clematis* plant named 'Zoqum' as herein illustrated and described.

* * * * *